United States Patent

Klose et al.

[11] Patent Number: 4,960,928
[45] Date of Patent: Oct. 2, 1990

[54] 1-HYDROXY-OMEGA-(ALKYL- OR ARYLPHOSPHINICO)ALKANE-1,1-DIPHOSPHONIC ACIDS, SALTS THEREOF, AND PROCESSES FOR THE PREPARATION OF THESE COMPOUNDS

[75] Inventors: Werner Klose, Erftstadt; Helmut Klemp, Kerpen, both of Fed. Rep. of Germany

[73] Assignee: Hoechst Aktiengesellschaft Knapsack, Hurth Knapsack, Fed. Rep. of Germany

[21] Appl. No.: 308,840

[22] Filed: Feb. 9, 1989

[30] Foreign Application Priority Data

Feb. 24, 1988 [DE] Fed. Rep. of Germany ....... 3805644

[51] Int. Cl.$^5$ ................................ C07F 9/38
[52] U.S. Cl. ......................... 562/21; 562/22; 562/817; 562/876
[58] Field of Search ............................ 562/21

[56] References Cited

U.S. PATENT DOCUMENTS 4,440,646  4/1984  Budnick ........................... 562/21
4,892,679  1/1990  Blum et al. ....................... 562/21

Primary Examiner—Mukund J. Shah
Assistant Examiner—E. Bernhardt
Attorney, Agent, or Firm—Connolly and Hutz

[57] ABSTRACT

The present invention relates to 1-hydroxy-ω-(alkyl- or arylphosphinico)alkane-1,1-diphosphonic acids of the general formula I

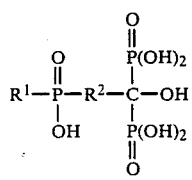

and to the salts of these acids of the general formula II

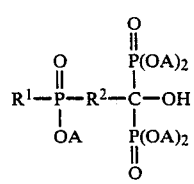

where, in these formulae, $R^1$ denotes an alkyl radical having 1 to 6 carbon atoms, a cycloalkyl radical having 5 to 7 carbon atoms or an aryl radical having 6 to 10 carbon atoms, $R^2$ denotes a straight-chain or branched alkylene radical having 1 to 6 carbon atoms and A denotes a monovalent equivalent of a cation of an inorganic or organic base. In addition, processes are described for the preparation of these novel compounds.

1 Claim, No Drawings

1-HYDROXY-OMEGA-(ALKYL- OR ARYLPHOSPHINICO)ALKANE-1,1-DIPHOSPHONIC ACIDS, SALTS THEREOF, AND PROCESSES FOR THE PREPARATION OF THESE COMPOUNDS

The invention relates to 1-hydroxy-ω-alkyl- or arylphosphinico)alkane-1,1-diphosphonic acids and salts thereof of the formulae I and II below, and to processes for the preparation of these novel compounds. In these formulae I and II:

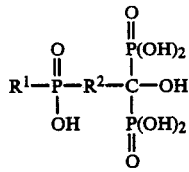

I

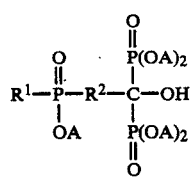

II $R^1$ denotes an alkyl radical having 1 to 6 carbon atoms, a cycloalkyl radical having 5 to 7 carbon atoms or an aryl radical having 6 to 10 carbon atoms, $R^2$ denotes a straight-chain or branched alkylene radical having 1 to 6 carbon atoms and A denotes a monovalent equivalent of a cation of an inorganic or organic base.

Alkanediphosphonic acids of the formula I are obtained by reacting carboxyalkylphosphinic acids of the general formula III

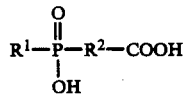

III in which $R^1$ and $R^2$ have the same meaning as in the general formula I, with phosphonylating agents, conditioning the reaction product at 100° to 160° C., and hydrolyzing the primary product formed.

Suitable phosphonylating agents here are primarily the agents known for phosphonylations, such as, for example, phosphorous acid,
phosphorus trichloride,
phosphorus tribromide,
oligo- and polyphosphorous acids and
phosphorous anhydride (tetraphosphorus hexoxide) or mixtures of these compounds.

Furthermore, alkanediphosphonic acids of the formula I are obtained when phosphorous acid is reacted either with a mixed cyclic carboxylic phosphinic anhydride of the general formula IV

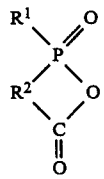

IV or with the double acid chloride of a carboxyalkylphosphinic acid of the general formula V

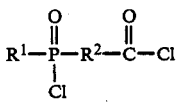

V the reaction product is subsequently conditioned at 100° to 160° C., analogously to the reaction of the free carboxyalkylphosphonic acid, and the primary product obtained is hydrolyzed.

In the formulae IV and V, $R^1$ and $R^2$ have the meaning given above in formula I.

When cyclic carboxylic phosphinic anhydrides of the general formula IV are used as a starting material, it is advisable, in order to increase the yield, to carry out the reaction in the presence of acid anhydrides, in particular anhydrides of phosphoric acid, such as polyphosphoric acid or $P_2O_5$.

To prepare salts of the abovementioned formula II, the hydrolyzate produced in each case in the manner described on hydrolysis of the primary products is neutralized using an inorganic or organic base whose cation corresponds to the cation A in the formula II.

In general terms, the preparation of the acids and salts according to the invention is carried out by initially mixing the reaction components with one another at temperatures between 0° and 100° C., preferably between 20° and 80° C., with exclusion of air and moisture, where the reactants can be added in any sequence in time. The temperature of the reaction mixture can be held in the range selected by regulating the metering rate of one of the reaction components or alternatively by heating or cooling.

In order to complete the reaction, the reaction mixture, if appropriate after an initial phase, which may proceed exothermically under certain circumstances, has subsided — and, when halogen-containing starting materials are used, with decreasing evolution of hydrogen halide — is conditioned for 3 to 30, preferably 5 to 20, hours at temperatures between 100° and 160° C., preferably between 130° and 150° C., with constant mixing. The primary product, which is generally highly viscous and usually solidifies to form a glassy material on cooling to room temperature, is taken up in water and, if appropriate after addition of small amounts of a strong mineral acid, heated to boiling in order to cleave by hydrolysis any condensed species and acid halide groups which may be present in the reaction product Separation of the acids of the formula I from unreacted starting components and any byproducts is expediently carried out by precipitating sparingly soluble salts with the inorganic or organic bases from solutions of the hydrolyzate in water or in mixtures of water with water-miscible organic solvents. The corresponding free acids of the formula I can be obtained in the H. form from the salts of the formula II, for example by treating the solutions with cation exchangers.

As bases which are suitable for this purpose, it is advisable to employ the hydroxides of alkali metal or alkaline earth metals or organic bases, such as, for example, melamine, guanidine, urea, aniline and others.

The compounds prepared according to the invention can be used as complexing agents for polyvalent metal ions, as sequestering agents in water treatment or as an additive for toothpastes for preventing tartar formation (so-called "antitartar agents").

EXAMPLE 1

Reaction of 2-methyl-2,5-dioxo-1,2-oxaphospholane (a compound of the general formula IV) with phosphorous acid 40.2 g (0.3 mol) of 2-methyl-2,5-dioxo-1,2-oxaphospholane and 49.2 g (0.6 mol) of phosphorous acid were melted at 80° to 100° C. in an $N_2$ atmosphere with exclusion of moisture in a glass flask fitted with stirrer. The reaction mixture was then heated to 150° C. over the course of one hour and stirred at this temperature for 10.5 hours. A sample was removed at this time and dissolved in water, and the solution obtained was boiled to effect hydrolysis of any acid anhydride functions which might be present. According to the $^{31}P$ NMR spectrum recorded on the hydrolyzate, about 47% of the 2-methyl-2,5-dioxo-1,2-oxaphospholane employed had reacted to form 1-hydroxy-3-(methyl-phosphinico)-propane-1,1diphosphonic acid ($^{31}P$ NMR signals: phosphinic acid group 57.5 ppm, phosphonic acid groups 17.2 ppm).

A further 49.2 g (0.6 mol) of phosphorous acid were then added to the reaction mixture, and the flask contents were stirred at 150° to 160° C. for a further 19 hours. The degree of reaction to 1-hydroxy-3-(methylphosphinico)propane-1,1-diphosphonic acid, based on the amount of 2-methyl-2,5-dioxo-1,2-oxaphospholane employed, was 58%.

EXAMPLE 2

Reaction of 2-methyl-2,5-dioxo-1,2-oxaphospholane (a compound of the general formula IV) with phosphorous acid 33.5 g (0.25 mol) of 2-methyl-2,5-dioxo-1,2oxaphospholane and 41 g (0.5 mol) of phosphorous acid were melted at 80° C. in an $N_2$ atmosphere with exclusion of moisture in a glass flask fitted with stirrer, and heated to 150° C. over the course of 30 minutes with constant stirring. After a reaction time of 4.5 hours at 150° C., a sample was removed, dissolved in water and hydrolyzed by boiling the aqueous solution According to the $^{31}P$ NMR spectrum recorded on the hydrolyzate, about 30% of the 2-methyl-2,5-dioxo-1,2-oxaphospholane employed had reacted to form 1-hydroxy-3-(methvl-phosphinico)propane-1,1diphosphonic acid ($^{31}P$ NMR signals phosphinic acid group 57.5 ppm, phosphonic acid groups 17.2 ppm).

67 g (0.2 mol) of polyphosphoric acid ($P_2O_5$ content about 84% by weight) were subsequently added dropwise to the reaction mixture at a temperature of 150° C., and the mixture thus obtained was kept at this temperature for 24 hours. After cooling to room temperature, the reaction mixture was in the form of a highly viscous, pale yellow material. The product obtained after hydrolytic work-up contains 1-hydroxy-3-(methylphosphinico)propane-1,1diphosphonic acid (yield 75%, based on the 2-methyl-2,5-dioxo-1,2-oxaphospholane employed) in addition to unreacted phosphorous acid, methyl-2-carboxyethylphosphinic acid resulting from hydrolysis of the unreacted oxaphospholane, and orthophosphoric acid formed from the polyphosphoric acid.

EXAMPLE 3

Reaction of 2-(chlorocarbonyl)ethylmethylphosphinic acid chloride (a compound of the general formula V) with phosphorous acid 378 g (2 mol) of 2-(chlorocarbonyl)ethylmethylphosphinic acid chloride

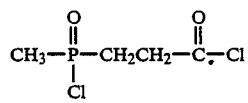

were introduced into a 2 l stirred flask, and 328 g (4 mol) of anhydrous phosphorous acid were introduced in portions over the course of 90 minutes with stirring, during which evolution of hydrogen chloride gas commenced.

The temperature of the reaction mixture was kept at 35 to 40° C. during introduction of the phosphorous acid if necessary by external cooling of the reaction vessel.

After evolution of hydrogen chloride had subsided, the temperature of the reaction mixture was increased slowly to 130° C., during which evolution of hydrogen chloride continued, and the reaction mixture was kept at 130° C. for 15 hours with continued stirring 560 g of a highly viscous primary product which solidifies on cooling to form a glassy material were obtained; the product was taken up in 560 g of water and refluxed for one hour. According to the $^{31}P$ NMR spectrum, about 70% of the total phosphorus content in the solution obtained are in the form of 1-hydroxy-3-(methylphosphinico)propane-1,1diphosphonic acid.

EXAMPLE 4

Preparation of the pentaguanidinium salt of 1-hydroxy-3-(methylphosphinico)propane-1,1-diphosphonic acid 300 ml of the hydrolyzate solution obtained in accordance with Example 3 and containing 38.1% by weight of 1-hydroxy-3-(methylphosphinico)propane-1,1-diphosphonic acid were diluted with 540 g of water and adjusted to a pH of 9.5 by adding guanidinium carbonate while monitoring the operation by means of a pH electrode. The clear solution obtained was poured, with stirring, into a mixture of 4,250 ml of methanol and 940 ml of water, and the resultant precipitate was filtered off after remaining under the mother liquor for 24 hours and washed with an acetone/water mixture in the volume ratio 4:1.

It was possible to obtain a second fraction of the salt by adding 1,700 ml of ethanol to the filtrate; this second fraction was dried, together with the precipitate formed initially, at 65° C. and a pressure of 7 mbar. 218 g of a solid remained; according to the results of analytical investigations, this solid is the pentaguanidinium salt of 1-hydroxy-3-(methylphosphinico)propane-1,1diphosphonic acid containing 3 moles of water of crystallization.

Empirical formula: $C_9H_{38}O_9N_5P_3 \cdot 3H_2O$,

Values calculated: N=32.5%; P=14.4%; H₂O=8.9%.

Values found: N=31.5%; P=13.9%; H₂O=8.2%

$^{31}$P NMR spectrum

=+46 ppm (phosphinic acid group, 33% P of the total P)

+18 ppm (phosphonic acid groups, 67% P of the total P)

The yield, based on the 1-hydroxy-3-(methylphosphinico)-propane-1,1-diphosphonic acid present in the hydrolyzate solution, is 88%.

EXAMPLE 5

Reaction of phosphorous acid with 2-(chlorocarbonyl)-ethylmethylphosphinic acid chloride 336 g (4.1 mol) of anhydrous phosphorous acid were melted at about 70° C. in a 2 l stirred flask with exclusion of moisture and with blanketing by a slow stream of nitrogen. 378 g (2 mol) of 2-(chlorocarbonyl)ethylmethylphosphinic acid chloride were added dropwise to this melt with constant stirring over the course of 2.5 hours, the temperature of the reaction mixture varying between 65° and 80° C.

When the evolution of hydrogen chloride which commences initially had subsided, the flask contents were heated to 130° C. and stirred for 20 hours at temperatures between 125° and 130° C. After cooling to room temperature, the weight of the flask contents was 579 g. The reaction product was subsequently refluxed for 25 minutes with the same weight of water with addition of 14 g of concentrated hydrochloric acid. The $^{31}$P NMR spectrum of the solution obtained indicated that 81% of the phosphorus employed was in the form of 1-hydroxy-3-(methylphosphinico)propane-1,1-diphosphonic acid.

EXAMPLE 6

Preparation of a monosodium salt of 1-hydroxy-3-(methylphosphinico)propane-1,1-diphosphonic acid 100 g of the aqueous solution obtained in accordance with Example 5 and containing 41% of 1-hydroxy-3-(methylphos-phinico)propane-1,1-diphosphonic acid are diluted with 200 ml of water and 2,000 ml of ethanol and adjusted to a pH of 3.65 by adding 65 g of 15% strength sodium hydroxide solution The resultant precipitate was kept under the mother liquor for 24 hours, slurried in methanol after decantation of the mother liquor, filtered and washed with acetone. The filter cake was dissolved in a little water with warming and re-precipitated by pouring the solution into plenty of methanol. After re-filtration and washing, the precipitate was dried at 110° C to constant weight. 41 g of a monosodium salt containing one mole of water of crystallization were obtained. This corresponds to a yield of 87%, based on the 1-hydroxy-3-(methylphosphinico)-propane-1,1-diphosphonic acid present in the starting solution.

Empirical formula: $C_4H_{12}O_9P_3Na \cdot H_2O$

Values calculated: 27.5% of P; 6.8% of Na

Values found: 27 3% of P; 7.0% of Na

EXAMPLE 7

Reaction of 3-carboxypropylmethylphosphinic acid with a mixture of phosphorous acid and phosphorus trichloride 29.1 g (175 mmol) of 3-carboxyprop-vlmethylphosphinic acid and 23.9 g (291 mmol) of phosphorous acid were melted at 70° C. in an N₂ atmosphere with exclusion of moisture in a 0.25 l stirred flask. 28.0 g of phosphorus trichloride (204 mmol) were added dropwise to this mixture over the course of 30 minutes at a temperature of the reaction mixture of 65° to 70° C. The reaction mixture was then heated to 135° C. with constant stirring When the evolution of hydrogen chloride which commenced on heating was complete, the mixture was stirred at a temperature of 135° C. for a further 24 hours. 54.5 g of a highly viscous primary product which solidifies on cooling to form a glassy material were obtained; this product was taken up in 54.5 g of water and refluxed for 1 hour. According to the $^{31}$P NMR spectrum, about 60% of the total phosphorus content in the solution obtained are in the form of 1-hydroxy-4-(methylphosphinico)butane-1,1-diphosphonic acid.

EXAMPLE 8

Preparation of a disodium salt of 1-hydroxy-4-(methyl-phosphinico)butane-1,1-diphosphonic acid 80 g of the aqueous solution obtained in accordance with Example 7 and containing 29.6% by weight of 1-hydroxy-4-(methylphosphinico)butane-1,1-diphosphonic acid were diluted with 80 ml of water and 1000 ml of methanol and adjusted to a pH of 3.9 by adding 25% strength by weight sodium hydroxide solution. The resultant white precipitate was filtered off after 24 hours and washed with a little acetone. The filter cake was dissolved in a little water with warming and stirred into 800 ml of hot methanol. The resultant precipitate was filtered off after 24 hours, washed with methanol and dried at 110° C. to constant weight.

33 g of a white solid were obtained; according to the results of analytical investigations, this solid is the disodium salt of 1-hydroxy-4-(methylphosphinico)butane-1,1-diphosphonic acid containing 2 moles of water of crystallization:

Empirical formula $C_5H_{13}O_9P_3Na_2 \cdot 2 H_2O$

Values calculated 23.7% of P; 11.7% of Na

Values found 24.6% of P; 10.9% of Na.

$^{31}$P NMR spectrum 54.5 ppm (phosphinic acid group, 33.8% P of the total P)

18.5 ppm (phosphonic acid groups, 64% P of the total P).

We claim:

1. A 1-hydroxy-ω-(alkyl- or arylphosphinico)alkane-1,1diphosphonic acid of the formula I $$R^1-\underset{\underset{OH}{|}}{\overset{\overset{O}{\|}}{P}}-R^2-\underset{\underset{P(OH)_2}{|}}{\overset{\overset{P(OH)_2}{|}}{C}}-OH \qquad I$$

or a salt of this acid of the formula II

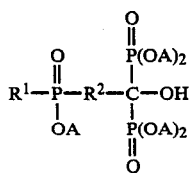
where, in these formulae, $R^1$ denotes an alkyl radical having 1 to 6 carbon atoms, a cycloalkyl radical having to 7 carbon atoms or an aryl radical having 6 to 10 carbon atoms, $R^2$ denotes a straight-chain or branched alkylene radical having 1 to 6 carbon atoms and A denotes a monovalent equivalent of a cation of an inorganic or organic base.
* * * * *